United States Patent
Holyoake

(10) Patent No.: US 7,673,501 B2
(45) Date of Patent: Mar. 9, 2010

(54) MOISTURE DETECTION

(76) Inventor: Ian Conrad Holyoake, 70 Churchill Rd., Howick, Auckland (NZ) 1704

( * ) Notice: Subject to any disclaimer, the term of this patent is extended or adjusted under 35 U.S.C. 154(b) by 232 days.

(21) Appl. No.: 11/573,087

(22) PCT Filed: Aug. 2, 2005

(86) PCT No.: PCT/NZ2005/000193

§ 371 (c)(1),
(2), (4) Date: Feb. 1, 2007

(87) PCT Pub. No.: WO2006/014111

PCT Pub. Date: Feb. 9, 2006

(65) Prior Publication Data

US 2007/0251318 A1    Nov. 1, 2007

(30) Foreign Application Priority Data

Aug. 2, 2004 (NZ) ................... 534447

(51) Int. Cl.
G01N 5/02 (2006.01)
(52) U.S. Cl. .......................... 73/73; 73/866.5
(58) Field of Classification Search ............ 73/73, 73/866.5

See application file for complete search history.

(56) References Cited

U.S. PATENT DOCUMENTS 2,754,378 A * 7/1956 Ohlheiser .............. 338/35
4,655,076 A * 4/1987 Weihe et al. ............ 73/73
5,730,024 A * 3/1998 Sahlen ................. 73/73
5,922,939 A * 7/1999 Cota .................. 73/29.01
7,231,815 B2 * 6/2007 Kanare ................. 73/73
2004/0055402 A1 * 3/2004 Pensis et al. ............ 73/866.5

FOREIGN PATENT DOCUMENTS

DE      4427244 A1 * 2/1996
DE     10250750 A1 * 5/2004

* cited by examiner

Primary Examiner—Hezron Williams
Assistant Examiner—Rodney T Frank
(74) Attorney, Agent, or Firm—Jeffrey D. Moy; Weiss & Moy, P.C.

(57) ABSTRACT

A method of retro-fitting a moisture detection fitting in the wall of a building in accordance with the following steps: forming a space which proceeds into the wall; and inserting the moisture detection fitting into the space such that a probe of the fitting: 1) presses into timber framing within the wall, or 2) stops short of timber framing within the wall but contacts a moisture absorbent filler forming part of the fitting and wherein the filler can absorb moisture from the timber framing. The moisture detection fitting being fitted substantially permanently such that when it is in use a moisture detection device can be detachably connected to the fitting outside the wall and use the probes, and if appropriate the filler, to measure a moisture content of the timber framing.

9 Claims, 6 Drawing Sheets

MOISTURE DETECTION

FIELD OF INVENTION

This invention relates to means for detecting moisture in a building.

BACKGROUND

It is known that moisture can intrude into the wall space of a building, for example between the external cladding and internal lining of a house, and cause significant damage. It is an object of a preferred form of the present invention to provide means suitable for use in detecting unacceptable levels of moisture within a wall space, or to provide the public with a useful choice.

The term "comprising" or derivatives thereof (eg "comprises"), if and when used herein, should be interpreted non-exclusively—eg if used in relation to a specific combination of features it should not be taken to exclude the possibility of there also being additional unspecified features.

SUMMARY OF INVENTION

According to one aspect of the invention there is provided a method of retro-fitting a moisture detection fitting in the wall of a building in accordance with the following steps: forming a space which proceeds into the wall; and inserting the moisture detection fitting into the space such that a probe of the fitting: 1) presses into timber framing within the wall, or 2) stops short of timber framing within the wall but contacts a moisture absorbent filler forming part of the fitting and wherein the filler can absorb moisture from the timber framing. The moisture detection fitting is fitted substantially permanently such that when it is in use, a moisture detection device can be detachably connected to the fitting outside the wall and use the probes, and if appropriate the filler, to measure a moisture content of the timber framing.

Preferably the moisture detection fitting has two substantially identical or similar probes and the fitting is fitted with both of these arranged with respect to the framing as set out above.

Preferably the probe, or if appropriate the probes, is or are each in the form of an elongate pin.

Preferably the fitting has an end plate which substantially conceals the space referred to at step a) when the fitting is fitted.

Preferably the fitting has a plurality of plug holes to facilitate connection of the moisture detection device.

According to a further aspect of the invention there is provided a moisture detection fitting suitable for use in the method set out above in connection with option b) ii), the fitting having an elongate body substantially housing and/or supporting at least a pair of probes and also housing a moisture absorbent filler, the probes extending from at or adjacent a first end of the body to the filler which is at or adjacent a second end of the body.

According to a further aspect of the invention there is provided a moisture detection fitting suitable for use in the method set out above in connection with option b) i), the fitting having an end plate at a first end thereof, an elongate body extending from the end plate while at the same time substantially housing and/or supporting at least a pair of probes, the probes extending from at or adjacent the first end of the body to a point beyond a side or second end of the body, the probes being of sufficient strength to enable them to be forced into or against timber wall framing to facilitate the taking of moisture readings for the framing.

Preferably the elongate body is narrower than the end plate.

BRIEF DESCRIPTION OF THE DRAWINGS

Some preferred forms of the invention will now be described by way of example and with reference to the accompanying drawings, of which.

DETAILED DESCRIPTION

Figure 1:
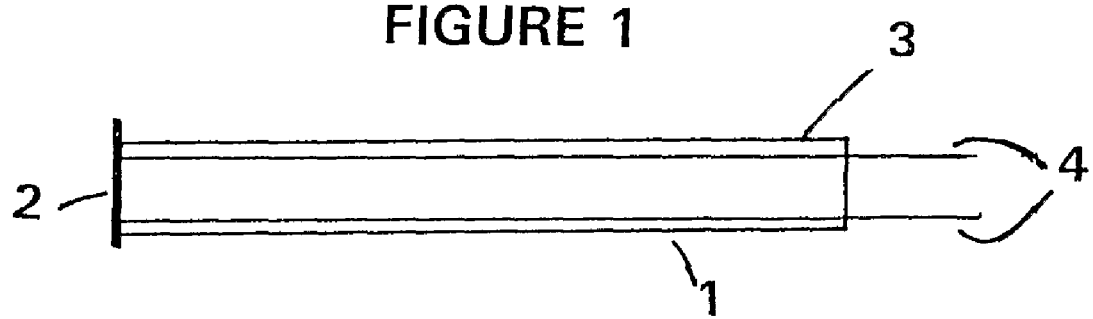
FIG. 1: is a side cross section of a moisture detection fitting.
Figure 2:
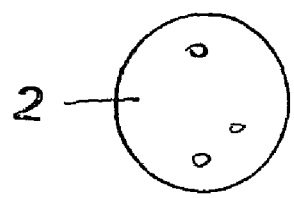
FIG. 2 FIG. 2 is a face view of an end plate forming part of the fitting.
Figure 2A:
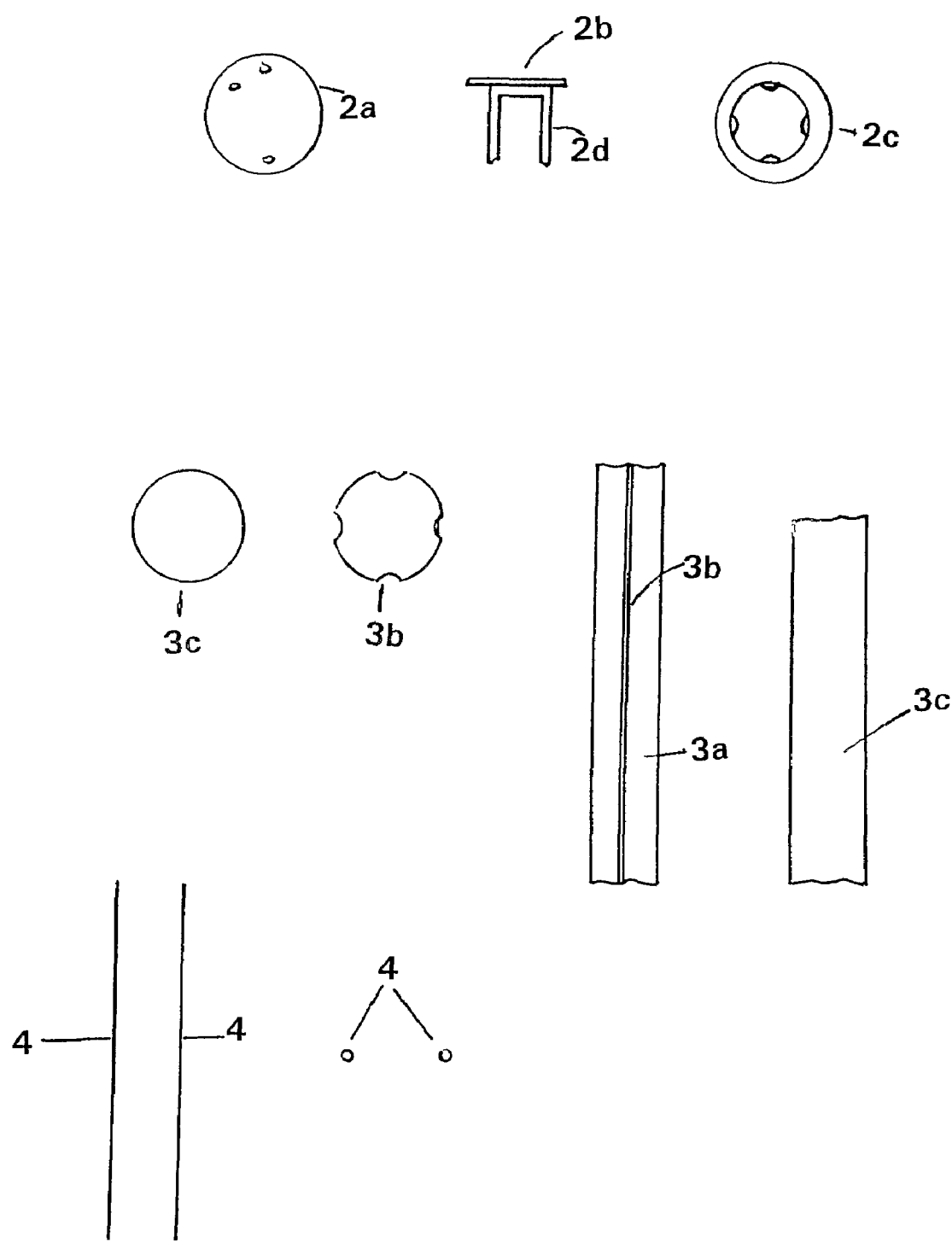
FIG. 2a shows parts of the fitting in a disassembled sate.

Referring to FIG. 1, a moisture detection fitting 1 has an end plate 2 and an elongate body 3 supportively housing a pair of probes 4. A face view of the end plate 2 is shown in FIG. 2. FIG. 2a shows the parts of the fitting 1 in end and side views in a disassembled state. The end plate 2 is shown in top end 2a, side 2b, and bottom end 2c views. The body 3 comprises an inner sleeve 3a having four slots 3b and a tubular outer protective sleeve 3c. The slots 3b each receive a respective one of four legs 2d of the end plate 2.

Figure 3:
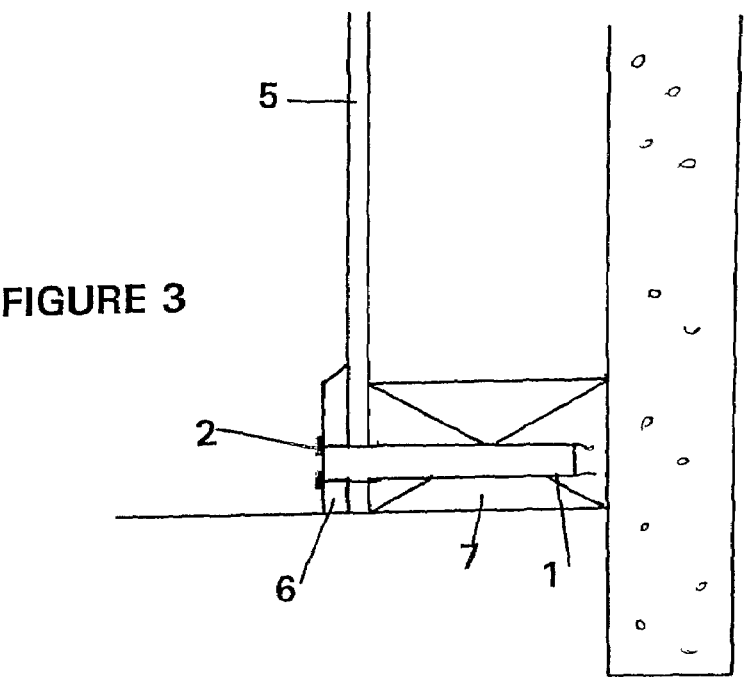
FIG. 3 is a cross sectional view showing the fitting installed within the interior side of the wall of a wall building.

Referring to FIG. 3, the fitting 1 can be installed in a building, for example a house, by drilling a hole in the interior lining 5, the skirting board 6, and the timber framing 7 of a wall. The fitting 1 is then pushed into the hole until the two probes 4 stab into the timber framing. The hole is thus drilled long enough to accommodate the fitting's elongate body 3 but not the probes 4. The probes create their own space in the framing. The end plate 2 rests against the wall as shown in FIG. 3 to overlap and conceal the hole to give an aesthetically pleasing appearance. A moisture meter (not shown) can be plugged into a connection just inside the end plate to electrically connect the meter with the probes 4. The arrangement is such that the moisture meter can, by way of the probes 4, take readings of the moisture content of the timber framing 7.

Figure 4:
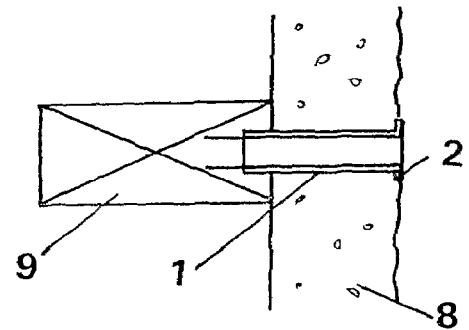
FIG. 4 is a cross sectional view showing the fitting installed within the exterior side of the wall of a wall building.

FIG. 4 shows the fitting 1 when installed in a similar fashion to FIG. 3, but in the exterior of the wall of a building. The exterior cladding is shown at 8 and the wall's internal timber framing at 9.

Figure 5:
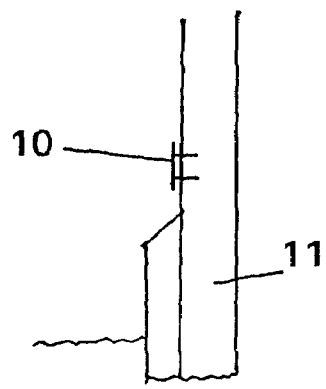
FIG. 5 is a cross sectional view of an alternative moisture detection fitting installed in the interior side of a wall lining, FIG. 6 provides side cross section views of various alternative moisture detection fittings.

FIG. 5 shows an alternative moisture detection fitting 10 which is similar to that described above, but without the elongate body 3. The fitting 10 can be pressed directly into relatively soft interior wall linings 11 (eg Gib board) to enable moisture readings thereof (ie as opposed to measuring the moisture content of wall framing).

Figure 6:
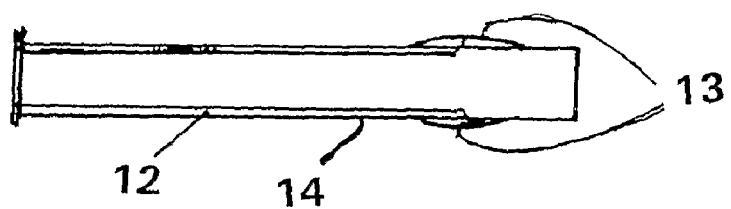
Figure 6:
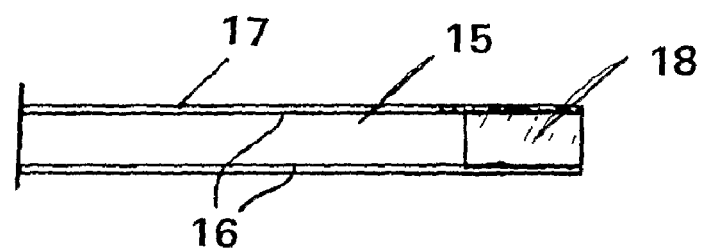
Figure 6:
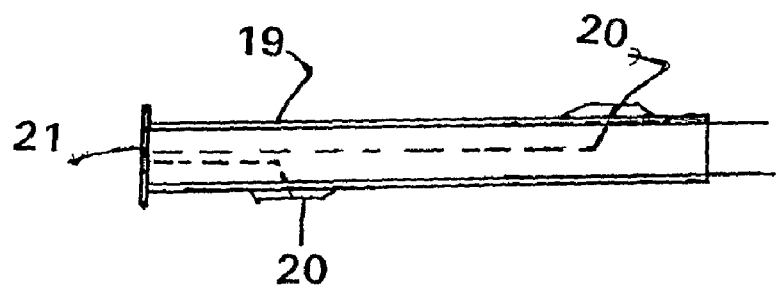
Figure 6:
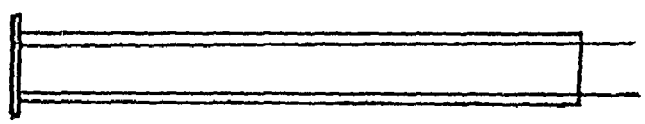
Figure 6:
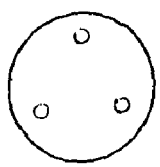

FIG. 6 shows alternative ways of forming a moisture detection fitting similar to that described with reference to FIG. 1. The first alternative 12 has a pair of probes 13 at the sides of the elongate body 14 rather than at the ends. The probes 13 may not be sharp but nonetheless provide an effective contact with timber framing to enable moisture readings thereof. The hole for the fitting 12 may be formed slightly narrower than the probes 13 so that the probes force a very tight contact with the framing when installed.

With the second alternative 15 the probes 16 stop short of the end of the elongate body 17. As shown, the probes 16 end within an absorbent filler 18 which proceeds to, and optionally beyond, the end of the elongate body 17. The filler may comprise chalk, balsa wood, a synthetic material, or any suitable substance. Moisture from the framing is absorbed in the filler 18 and the probes enable moisture readings from the filler 18. Such readings are reflective of the moisture content of the framing itself. The use of a filler 18 addresses some variable moisture readings resulting from the use of different types of timber framing (eg pine versus cedar, etc) or interference from adjacent building components (eg nails, metallic reinforcing, etc).

With further reference to FIG. 6, the third alternative 19 is similar to that described for the first alternative 12, but with the probes 20 set at different distances from the cover plate 21. This facilitates moisture readings at more than one location and may enable one to determine a moisture gradient across specific timber framing.

Figure 7:
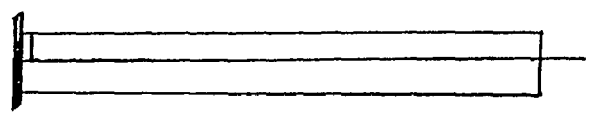
FIG. 7 shows the side and end of a moisture detection fitting formed with two hinged parts.
Figure 7:
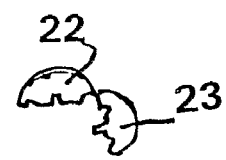

In some embodiments of the invention the elongate body and end plate of each moisture detection fitting described above for FIGS. 1, 2, 3, 4 and 6 may be formed from a suitable plastic material. As demonstrated at FIG. 7, the arrangement may be such that in each case at least the elongate body is in two hinged parts 22, 23 which can be pressed together to give a finished elongate body.

Figure 8:
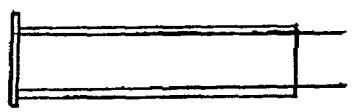
FIG. 8 shows a shortened moisture detection fitting.

FIG. 8 shows a shortened version of the moisture detection fitting.

Figure 9:
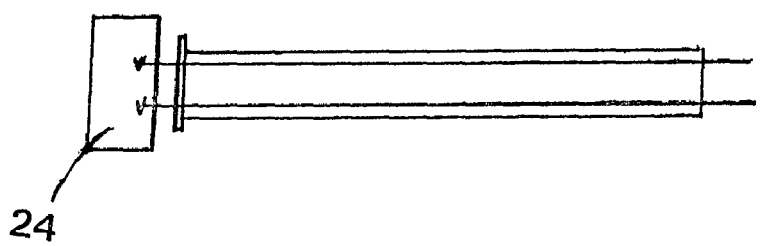
FIG. 9 shows a moisture detection fitting fitted with a recorder.

Referring to FIG. 9, the moisture detection fittings described above may be suitable for connection to an external (of the wall) recorder 24 which can transmit moisture readings (optionally wirelessly) and/or store these electronically. The recorder may communicate with an alarm system to alert a homeowner as to unacceptable levels of moisture within timber framing.

Figure 10:
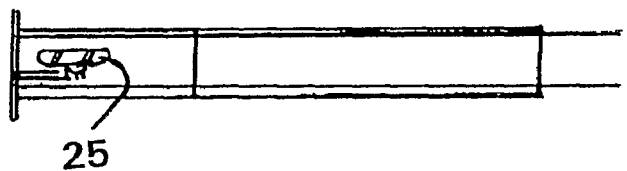
FIG. 10 shows a moisture detection fitting incorporating an identification device.

Referring to FIG. 10, the moisture detection fittings described above may have an electronic identification device 25 just behind the end plate or at another suitable position to assist in collating information when read and recorded by way of the fittings.

Figure 11:
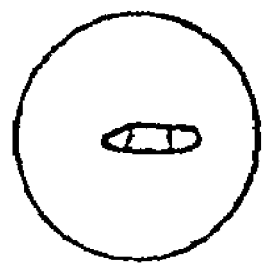
FIG. 11 shows various styles of optional end plates forming part of the a moisture detection fitting.
Figure 11:
Figure 11:
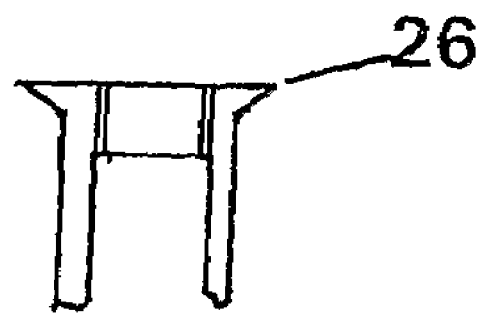

FIG. 11 demonstrates various optional end plates suitable for use as part of the invention. The end plates may be formed with tapered sides 26 to enable a counter sunk installation in a wall.

In some preferred embodiments of the invention the moisture detection fitting may have one, two, three, or more apertures for receiving the pins of a moisture meter. The invention is not limited to any particular number of these. Each aperture may be associated with a different probe depending on the desired application and the type of moisture meter used.

An advantage of preferred forms of the invention is that one can create a single cavity in the wall of a building and permanently retro-fit the moisture detection fitting for repeated use. This overcomes disadvantages in the prior art where moisture detection may involve creating a cavity or hole each time one needs to take a moisture reading. In the prior art each time a subsequent moisture reading is taken the cavity or hole created previously will have been exposed to air and thus may not allow an accurate and useful indication of moisture content of the wall, or if the hole or cavity has been repaired since the last moisture reading one needs to create a further cavity or hole. The invention allows one to permanently fit a fitting which enables ready connection of a moisture meter.

In some embodiments of the invention the fitting may be formed as described for FIG. 1, but with elongate probes extending well beyond the end of the elongate body which is opposite the end plate. Such probes are of sufficient length and ductility that they can be bent and maneuvered to a desired part of timber framing.

The electrodes used in the various embodiments of the invention described above may be in the form of metallic pins or the like. In some aspects of the invention the fitting may be wired or otherwise connected to other such fittings or electronic devices generally.

In some embodiments of the invention the fitting may also have probes for making temperature or other measurements/readings.

While some preferred forms of the invention have been described by way of example it should be appreciated that modifications and improvements can occur without departing from the scope of the following claims.

What is claimed is:

1. A method of retrofitting a moisture detection fitting in the wall of a building in accordance with the following steps:
   a) forming a space which proceeds into the wall,
   b) inserting the moisture detection fitting into the space such that a probe of the fitting:
      i) presses into timber framing within the wall, or
      ii) stops short of timber framing within the wall but contacts a moisture absorbent filler forming part of the fitting wherein the filler contacts the timber framing to absorb moisture from the timber framing,
   the moisture detection fitting being fitted substantially permanently such that when it is in use a moisture detection device can be detachably connected to the fitting outside the wall and use the probes, and if appropriate the filler, to measure a moisture content of the timber framing.

2. A method according to claim 1, wherein the moisture detection fitting has two substantially identical or similar probes and the fitting is fitted with both of these arranged with respect to the framing as set out in claim 1.

3. A method according to claim 1, wherein the probe is in the form of an elongate pin.

4. A method according to claim 1, wherein the fitting has an end plate which substantially conceals the space referred to at step a) when the fitting is fitted.

5. A method according to claim 1, wherein the fitting has a plurality of plug holes to facilitate connection of the moisture detection device.

6. A moisture detection fitting formed such that it is suitable for use in the method set out at claim 1 in connection with option b) ii), the fitting having an elongate body substantially housing and/or supporting at least a pair of probes and also housing a moisture absorbent filler, the probes extending from at or adjacent a first end of the body to the filler which is at or adjacent a second end of the body.

7. A moisture detection fitting formed such that it is suitable for use in the method set out at claim 1 in connection with option b) i), the fitting having an end plate at a first end thereof, an elongate body extending from the end plate while at the same time substantially housing and/or supporting at least a pair of probes, the probes extending from at or adjacent the first end of the body to a point beyond a side or second end of the body, the probes being of sufficient strength to enable them to be forced into or against timber wall framing to facilitate the taking of moisture readings for the framing.

8. A moisture detection fitting according to claim 7, wherein the elongate body is narrower than the end plate.

9. A method of retrofitting a moisture detection fitting which has two probes in the wall of a building in accordance with the following steps:
   a) forming a space which proceeds into the wall, and
   b) inserting the moisture detection fitting into the space such that both of the probes press into timber framing within the wall;

the moisture detection fitting having an end plate, an elongate body narrower than the end plate, and a plurality of plug holes;

the moisture detection fitting being fitted substantially permanently with the end plate substantially concealing the space, and such that when it is in use a moisture detection device can be detachably connected to the fitting outside the wall via the plug holes and use the probes to measure a moisture content of the timber framing.

* * * * *